(12) United States Patent
Meerbeek et al.

(10) Patent No.: US 10,241,738 B2
(45) Date of Patent: Mar. 26, 2019

(54) METHOD AND SYSTEM OF COMMUNICATION FOR USE IN HOSPITALS

(71) Applicant: KONINKLIJKE PHILIPS N.V., Eindhoven (NL)

(72) Inventors: Berent Willem Meerbeek, Eindhoven (NL); Jonathan David Mason, Waalre (NL); Dzmitry Viktorovich Aliakseyeu, Eindhoven (NL); Sanae Chraibi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 17 days.

(21) Appl. No.: 15/522,486

(22) PCT Filed: Oct. 30, 2015

(86) PCT No.: PCT/EP2015/075349
§ 371 (c)(1),
(2) Date: Apr. 27, 2017

(87) PCT Pub. No.: WO2016/071244
PCT Pub. Date: May 12, 2016

(65) Prior Publication Data
US 2017/0315774 A1    Nov. 2, 2017

(30) Foreign Application Priority Data
Nov. 6, 2014    (EP) .................................. 14191982

(51) Int. Cl.
*G06F 3/14* (2006.01)
*G16H 40/63* (2018.01)
(Continued)

(52) U.S. Cl.
CPC ............ *G06F 3/1454* (2013.01); *G06F 3/011* (2013.01); *G06F 3/013* (2013.01); *G06F 3/017* (2013.01);
(Continued)

(58) Field of Classification Search
None
See application file for complete search history.

(56) References Cited

U.S. PATENT DOCUMENTS

| 8,601,380 B2 | 12/2013 | Vaittinen |
| 2002/0044152 A1 | 4/2002 | Abbott |

(Continued)

FOREIGN PATENT DOCUMENTS

| CN | 201903695 | 7/2011 |
| WO | 2010/052548 | 5/2010 |

(Continued)

OTHER PUBLICATIONS

Nilsson, et al., "Using AR to support cross-organisational collaboration in dynamic tasks", Mixed and Augmented Reality, 2009.
(Continued)

*Primary Examiner* — Kenneth B Lee, Jr.

(57) ABSTRACT

A communication system for a plurality of users in an emergency room or operating room environment, in particular for use in hospitals, efficiently assists communication in a complex environment. The communication system for a plurality of users of wearable capturing devices includes a circuit (identification circuit) including program logic arranged to identify, by a second wearable device, and capture a viewpoint of the first wearable device; a circuit (exchange circuit) includes program logic arranged to cause the first wearable device wearer to exchange the captured viewpoint with the second wearable device wearer; and a circuit (projecting circuit) includes program logic arranged to provide the exchanged viewpoint by the second wearable device as an exchanged viewpoint to the second wearable device wearer.

16 Claims, 4 Drawing Sheets

(51) Int. Cl.
*G16H 80/00* (2018.01)
*G06F 9/451* (2018.01)
*G06F 3/01* (2006.01)
*G06F 19/00* (2018.01)
*G06T 11/60* (2006.01)

(52) U.S. Cl.
CPC .............. *G06F 9/451* (2018.02); *G06F 19/00* (2013.01); *G06F 19/3481* (2013.01); *G06T 11/60* (2013.01); *G16H 40/63* (2018.01); *G16H 80/00* (2018.01)

(56) References Cited

U.S. PATENT DOCUMENTS

| | | | |
|---|---|---|---|
| 2004/0169724 A1 | 9/2004 | Ekpar | |
| 2009/0074265 A1 | 3/2009 | Huang | |
| 2010/0325563 A1 | 12/2010 | Goldthwaite | |
| 2012/0057032 A1 | 3/2012 | Jang | |
| 2012/0206334 A1* | 8/2012 | Osterhout | G06F 1/163 345/156 |
| 2012/0293546 A1* | 11/2012 | Lahcanski | G06T 19/006 345/633 |
| 2013/0293468 A1* | 11/2013 | Perez | G06F 3/033 345/158 |
| 2015/0339453 A1* | 11/2015 | Richards | G06T 11/00 345/633 |

FOREIGN PATENT DOCUMENTS

| | | |
|---|---|---|
| WO | 2013/093906 | 6/2013 |
| WO | 2013/173793 | 11/2013 |
| WO | 2014/100688 | 6/2014 |
| WO | 2014/134196 | 9/2014 |

OTHER PUBLICATIONS

Lingard, et al., "Communication failures in the operating room: an observational classification of recurrent types and effects", Qual Saf Health Care. Oct. 2004;13(5):330-4.

* cited by examiner

METHOD AND SYSTEM OF COMMUNICATION FOR USE IN HOSPITALS

CROSS REFERENCE TO RELATED APPLICATIONS

This application is the U.S. National Phase application under 35 U.S.C. § 371 of International Application No. PCT/EP2015/075349, filed Oct. 30, 2015, published as WO 2016/071244 on May 12, 2016, which claims the benefit of European Patent Application Number 14191982.9 filed Nov. 6, 2014. These applications are hereby incorporated by reference herein.

FIELD OF INVENTION

The invention relates to a communication system for use in hospitals or primary care facilities, and in particular in intensive care units and emergency rooms or operating rooms. The invention also relates to a method of communicating and a computer program product for putting into effect such method.

DESCRIPTION OF THE PRIOR ART

In emergency rooms or operating room environments, communication skills and team play of the operating team are paramount. For example, an operating physician may act based on his cognition, experience and interaction with medical staff, but for instance yet fail to register a physiological signal that may otherwise be known to other members of the team, such as paramedics or co-working doctors. It is known, that even in such situations, team members are sometime not able to convey their observations to the operating doctor, for various reasons.

Also, participating members may be in optimal or less optimal condition to act and respond to calls from the team, which may sometimes be unnoticed and causing hazardous delay. All this puts substantial challenges for adequately responding to operating situations that require instant decisions taken under full stress, without optimum information.

In hectic emergency situations this may lead to a lack of overview, and/or lack of communication between team members in the operation room.

In other prior art systems, e.g. WO2013173793 a computer assisted role-play is described, where a computer may aid, together with camera registration in the interaction and evaluation of a medical team for assisting rescuers in performing and reviewing cardio-pulmonary resuscitation (CPR). By combining images a scene can be reconstructed in 3D. However, this system is not able to organize communication of the team members in a structured way, which will enhance the team interaction and timely identify vital information for successful responding to emergencies.

SUMMARY OF THE INVENTION

In one aspect, it is aimed to provide a communication system for a plurality of users in an emergency room or operating room environment, in particular for use in hospitals in order to efficiently assist in communication in a complex environment.

The communication system for a plurality of users of wearable capturing devices comprises a circuit (identification circuit) comprising program logic arranged to identify, by a second wearable device, the viewpoint of a user of the first wearable device; a circuit (exchange circuit) comprising program logic arranged to cause the first wearable device to exchange the captured viewpoint with the second wearable device; and a circuit (projecting circuit) comprising program logic arranged to provide the exchanged viewpoint to a user of the second wearable device.

In another aspect it is aimed to provide a communication method for a plurality of users in an emergency rooms or operating room environment, in particular for use in hospitals in order to efficiently assist in communication in a complex environment.

To this end, a method of communication is provided comprising capturing, by a first wearable device, a viewpoint of a user of the first wearable device; identifying, by a second wearable device, the viewpoint of the first wearable device; causing a user of the first wearable device to exchange the captured viewpoint with a second wearable device; and; providing the exchanged viewpoint to a user of the second wearable device.

For example, an operating doctor may pull a team members' view based on a confirmation, confirmed by either one of the members. For example, an exchange view may be pushed to the operating doctor, confirmed by either one of the members.

BRIEF DESCRIPTION OF THE DRAWINGS

The invention will be further elucidated in the figures.

DETAILED DESCRIPTION

Figure 1:
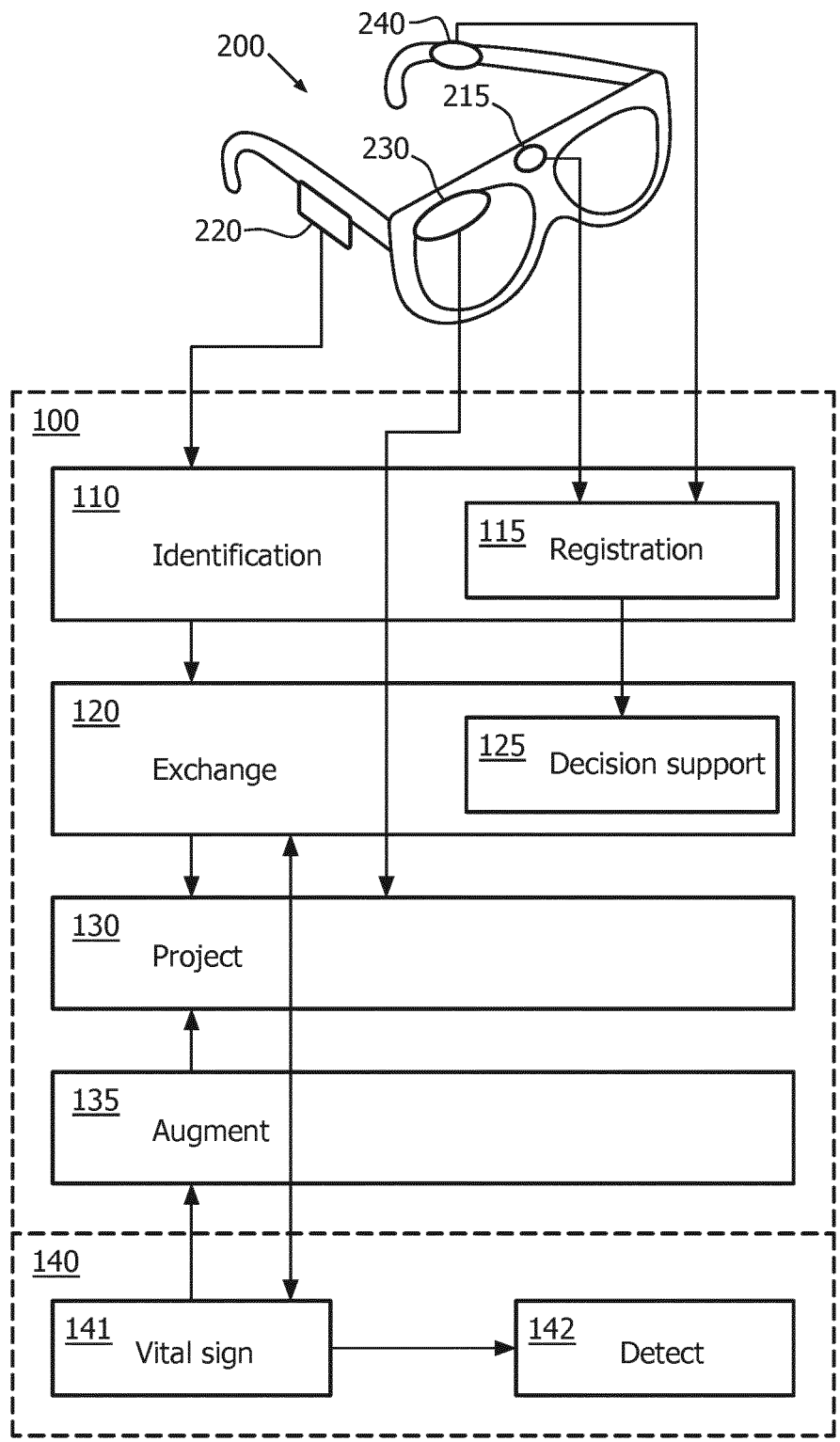
FIG. 1 shows a communication system for a plurality of users wearing head mounted capturing devices.

Unless otherwise defined, all terms (including technical and scientific terms) used herein have the same meaning as commonly understood by one of ordinary skill in the art to which this disclosure belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be further understood that the terms "comprises" and/or "comprising" specify the presence of stated features but do not preclude the presence or addition of one or more other features. All publications, patent applications, patents, and other references mentioned herein are incorporated by reference in their entirety. In case of conflict, the present specification, including definitions, will control.

The term "circuit" is used in a conventional way to signify any structural hardware or software arrangement having a capability of executing program logic in order to provide a certain basic function. A skilled person is typically aware of how to operate or implement a circuit in the context of the description, with processor elements elucidated here below. For example, an 'identification circuit' comprises hard/and or software elements dedicated to the purpose, as further illustrated here below, of identifying a viewpoint of another person's wearable device. For example, an 'exchanged circuit' comprises program logic arranged to causing a wearable device to exchange a captured viewpoint of said wearable device. The exchange circuit, to this end has connectivity devices that connect with corresponding devices of other wearable devices, in order to establish an exchange of viewpoints, when caused to do so. For example, a 'projecting circuit' has program logic arranged to project an exchanged viewpoint as an 'exchanged viewpoint', that is in addition to a persons' received viewpoint, more particular, his own viewpoint. This may be provided by separate projection or by integrating with virtual reality or augmented reality techniques, as further exemplified here below.

The term "program logic" is used in a conventional way to signify the operating instructions, which may be embodied in hardware and/or software structures, that control a circuit to the designated functional behavior.

The term "module" as in "augmented reality module" or "camera module" is used to emphasize the modular character of these units, i.e. the functionality of the system is separated into independent, interchangeable units. A "communication module" may be formed by a unit capable of communicating with the augmented reality module.

The term "user interface" may comprise one or more hardware elements configured to perform operational acts in accordance with the present systems and methods, such as to provide control signals to the various other module components. The processor may be a dedicated processor for performing in accordance with the present system or may be a general-purpose processor wherein only one of many functions operate for performing in accordance with the present system. The processor may operate utilizing a program portion, multiple program segments, or may be a hardware device utilizing a dedicated or multi-purpose integrated circuit. Any type of processor may be used such as a dedicated or shared one. The processor may include microcontrollers, central processing units (CPUs), digital signal processors (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

While example embodiments are shown for systems and methods, also alternative ways may be envisaged by those skilled in the art having the benefit of the present disclosure for achieving a similar function and result. E.g. some components may be combined or split up into one or more alternative components. Finally, these embodiments are intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the scope of the present systems and methods as set forth in the claims that follow. The specification and drawings are accordingly to be regarded in an illustrative manner and are not intended to limit the scope of the appended claims.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage.

The communication system as presently disclosed comprises an augmented reality module arranged to record a plurality of views in an multiple view context, wherein a plurality of viewers have different viewpoints recorded by respective viewing devices, formed by the step of identifying a selected viewer's viewpoint, causing the selected viewer to exchange his viewpoint and providing the selected viewpoint as an exchanged viewpoint to the viewer. Said viewing devices can also be referred to as wearable devices, wearable capturing devices, head mounted capturing devices or head mounted devices. In some instances, the view may be recorded by a wearable device, for example augmented reality glasses. In some instances a view may be caused to be exchanged by gaze detection by the wearable device.

Gaze detection may be provided by a head mounted device being provided with narrow coded beam that can be directed and impinges on another wearable device. For example an angled beam with an angle in a range of 1-5 degrees may be capable of providing a directionality that is able to easily target and identify a co-worker for exchanging a view.

Alternatively gaze detection can be provided by optical tracking methods where for example infrared light is reflected from the cornea and the pupil of a wearer of the wearable device and sensed by a camera or optical sensor. Gaze detection can also be provided by computer vision techniques that extract relevant facial features from a camera image that can be used to estimated gaze direction, for example head pose and direction of the nose. Alternatively, a view may be caused to be exchanged by speech processing. For instance, a view may be exchanged by a voice command such as: "Give me view of doctor Smith." In other instances, the view may be caused to be exchanged by a physiological signal registration. For instance, the physiological signal registration may be monitored by one of the team members, and when a physiological signal exceeds a certain level, his/her associated view may be caused to be exchanged. For instance, a physiological signal registration may also be associated with a team member. For example, if a team member experiences a predetermined reaction, such as heart rate increase or pupil dilation, such may be caused to exchange the view of that person. In many instances, the causing of exchanges may be accompanied by a confirmation protocol, which may be pushed or pulled.

Turning now to FIG. 1, there is illustrated a communication system 100 for a plurality of users wearing head mounted capturing devices 200. For example, the wearable device may be in the form of glasses as depicted or other suitable wearing equipment (band strap), which can be used for capturing and projecting views available for the person wearing the device. The capturing device is arranged to capture a viewpoint of a respective head mounted device wearer (not shown). In the Figure, schematically, signal lines are shown to explain on a generic level information processing between the processing circuits, in particular, identification circuit 110, exchange circuit 120 and projection circuit 130.

In the depicted example a controller 220 is arranged, which may be partly or wholly implemented in a second head mounted device, e.g. in the form of a hardware processor device. The controller may be connected to a central communication server or distributed system 100, e.g. by direct connectivity to another controller 220 arranged in another head mounted device. The projecting circuit operates with a projector 230, suitably integrated in the glasses 200.

Controller 220 may comprise a circuit called identification circuit 110 comprising program logic arranged to identifying, by the second head mounted device, the viewpoint of a first head mounted device. Controller 220 may furthermore comprise a circuit called exchange circuit 120 comprising program logic arranged to causing the first head mounted device wearer to exchange the viewpoint captured by the first head mounted device with the second head mounted device. The identification of the viewpoint of the first head mounted device is achieved by a registering circuit 115, which may be part of the identification circuit 110 or be communicatively connected thereto. The registering circuit 115 may comprise program logic arranged to register a predefined user gesture, physiological signal or speech, instruction command or other detection parameter to cause the first head mounted device to exchange the viewpoint of the first head mounted device with the second head mounted device. Also, the controller 220 comprises a circuit called projecting circuit 130 comprising program logic arranged to projecting the exchanged viewpoint by the second head mounted device as an exchanged viewpoint to the second head mounted device wearer.

Advantageously, but not necessarily projecting circuit 130 may be suitably integrated with an augmented reality module 135. The functionality of such modules is known per se in the art and typically combines reality vision with augmented vision, in such a way that the reality vision is augmented with additional information. For example, items that are in vision may be 'augmented' with additional relevant information depicted in a portion of a field of view. Augmented module 135 may additionally be provided with program logic arranged to stitch the exchanged viewpoint with a viewpoint of the second head mounted device in augmented reality. Stitching is an operation that is per se known to the skilled person and is directed to joining, via image processing, multiple images into a single image, where the images have transition zones that are suitably matched to each other by means of induction and extrapolation, or by means of intermediate images. Accordingly, a collection of multiple mobile camera or head mounted devices 200 may have multiple views to produce a stitched view that forms an aggregated view of an environment or to allow people to obtain another persons' perspective. Also, using information on the location and orientation of the mobile camera's images can be stitched from various perspectives in an aggregated view. This has the advantage that the wearer(s) of head mounted device 200 may access a stitched view thereby obtaining viewpoints of other people or combined views of multiple people while these images are being collected and centralized in a single aggregated view (see FIG. 4A).

Such an augmented view, wherein an exchanged viewpoint is projected simultaneously with a wearer's own viewpoint, preferably in a stitched form, can be useful in complex emergency situations like in operation rooms, where many people with multiple perspectives judge a certain emergency situation. However, this may also be applicable in other domains and applications where a stitched view from multiple mobile camera views provides meaningful information, e.g. search and rescue tasks, gaming, safety and security, outdoor/public area. Also, non-real time applications can be useful, for example for training purposes.

As further depicted in FIG. 1, advantageously but not necessarily exchanged views may be combined with physiological signal information. This may be beneficial when role-specific views are available by persons carrying out specific tasks. E.g.: a camera may create specific views based on the role of the person wearing the camera for example an IR view, zooming in/cutting out specific parts of body and specific physiological signals, for example physiological signals monitored by an anesthesiologist. By adopting a view of another person's role, a difficulty may be overcome to take perspectives of other team member to get holistic view/different view on the patient. To this end physiological signal monitoring module 140 may comprise physiological signal detectors 142. The detectors 142 are equipped with sensors 240 which may form part of the head mounted devices, or may be located on the patient. Program logic 142 is provided to convey said physiological signal information to the augmented reality module 135. The module 135 comprises logic to display said conveyed physiological signal information in the projecting device 230 in ways known to the skilled person. For example communication system 100 may be provided with instruction code to convey physiological signal information of an anesthesiologist to the operating doctor if any of these physiological signals would exceed a certain threshold, e.g. when saturation levels would be below a certain threshold value. Also, for example, register circuit 115 may be provided with instruction code to convey physiological signal information of a co-worker in addition to a co-workers view, if the worker would experience an unexpected change of physiological signal information, e.g. a pupil dilatation, heart rate or breathing rate that is out of bounds.

Thus another persons' capturing device may be obtained to analyze physiological measures (e.g. stress) of the caregivers. The capturing device may suggest a view from a caregiver that experienced an acute level of stress caused by seeing a problematic or abnormal event. To determine these stressful events, the capturing device may measure one or more physiological characteristics of the caregiver that indicate an increase in stress level (e.g. pupil dilation, heart rate variability). In case of these events, instead of the actual real time view, snapshots or a sequence of images surrounding the time of detecting the stress level.

Also, this may enhance real-time communication support in operation room. For example co-workers with corresponding head mounted devices may flag up issues via a gesture, speech or by touching the head mounted device to inform the others in the room of options. Should this be a safety critical situation, this first request can be filtered by the master viewer before passing on the information or concern to others in the situation. This way, hierarchical based errors where a doctor may not listen to the nurse can be overcome and provide the nurse with the ability to flag issues without unnecessary disturbance. This may overcome problems that during hectic emergency situations in operation rooms with many people in the room an operating doctor fails to have an overview or experiences a lack of communication between team members in the operation room.

Accordingly, the communication system 100 may have the exchange circuit 120 arranged to exchange a captured viewpoint of the first head mounted device 200 when a conveyed physiological signal value exceeds a threshold value. The physiological signal may be any signal indicative of stress or vitality, which may be important to register and may influence a clinical decision or exchange a captured view. The exchange circuit 120 may thereto be equipped with a rule-based decision support system 125 that may thereby automatically trigger the wearable device to produce a view, for example to signal a potentially dangerous situation (e.g. $SpO_2$ levels are too low). Such extension could include clinical analysis that analyses the registered input from the head mounted device (images, audio), in combination with data from connected monitoring devices (e.g. heart rate monitor) and electronic patient information records, to provide relevant information towards the doctor (on the head mounted device) during the surgical procedure. This could for example be a warning message if the microphone picks up that the doctor wants to give a particular medicine to the patient, but the information in the patient record indicates that the patient is allergic to this medicine.

Figure 2:
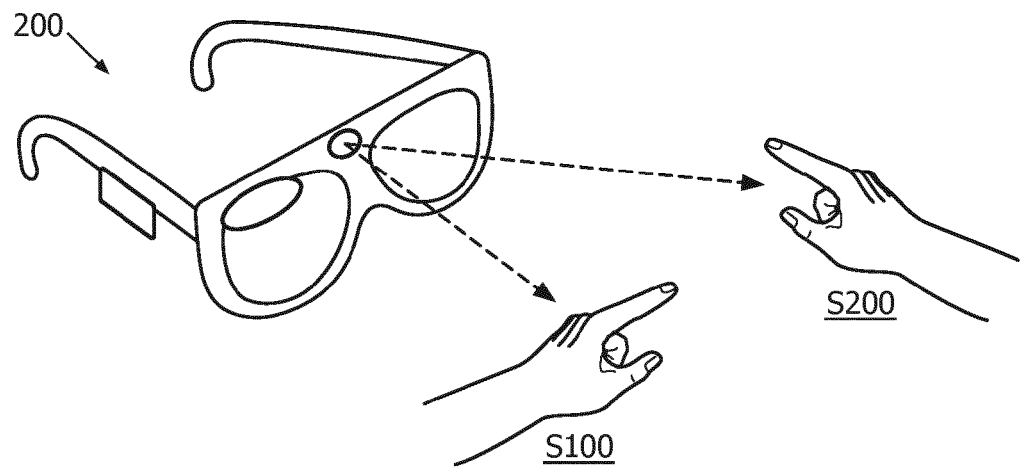
FIG. 2 shown a registering circuit, comprising program logic arranged to register a predefined user gesture.
Figure 2:
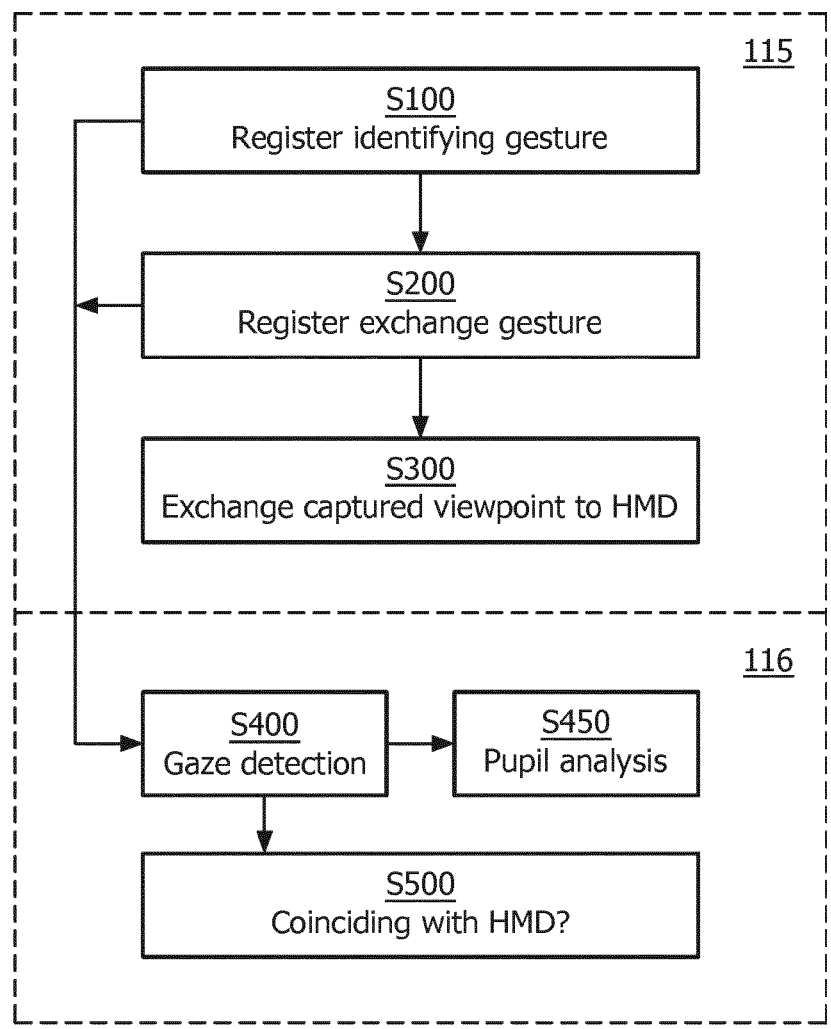

In more detail, in FIG. 2, it is shown how the registering circuit 115 of the second head mounted device, comprising program logic, is arranged to register a predefined user gesture called identifying gesture (S100). Thus, an identifying may be made by a person interested in obtaining another person's view, i.e. the viewpoint of the first head mounted device by hand, finger or eye gesture (S100) thereby identifying the viewpoint of the targeted head mounted device, i.e. of the first head mounted device, due for exchanging the captured view. Registering circuit 115 further comprises program logic 117 arranged to register another predefined user gesture called exchange gesture (S200). An exchange gesture (S200), confirming the identification, may then be used by causing the exchange circuit 120 of the second head mounted device to exchange (S300) the captured viewpoint of the confirming device, i.e. of the first head mounted device, to the second head mounted device. Confirmation may be provided by suitable exchange gestures (S200), such as a head bow, eye movement or other recognizable gestures, voice commands, touch, button press, etc. . . .

A wearer's gaze direction may be provided by known means, as briefly exemplified in the Figure. For example, projection device 230 may have an eye detector that monitors a person's pupil. Accordingly, gaze detection device 116 may comprise program logic arranged to perform pupil analysis S450 of a wearer of the head mounted device.

Figure 3:
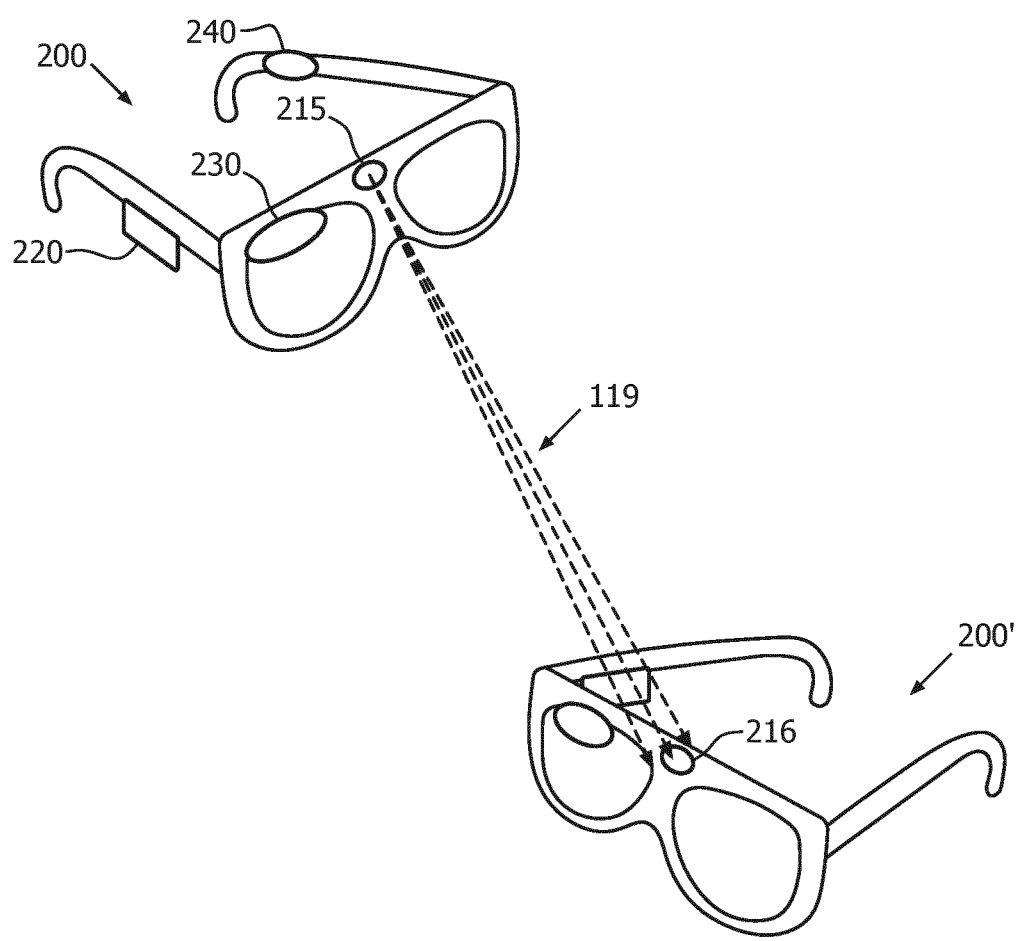
FIG. 3 shows a gaze detection device.

In an embodiment, further exemplified in FIG. 3, gaze detection device 116 can be equipped with a circuit called analyze circuit to analyze S400 a second wearers gaze direction; and a circuit to identify S500 the first head mounted device when the circuit detects that a second wearers gaze direction coincides with a location of the first head mounted device. Advantageously, comprises a directed coded beam transmitter 215. A narrow coded beam may be provided by an IR laser having some spreading, for example in a range of 1-5 degrees. Such a narrow beam has sufficient directionality to uniquely identify a head mounted device of a person of interest, in order to cause that device to exchange the captured viewpoint of its wearer. The coding can signify the requestor and for example, a request type, for example, signaling an authorization level for obtaining exchange information.

Similarly, the glasses 200 may be provided with a coded beam detector 216 to receive the directed coded beam 119. In this way gaze detection may be provided by transmitting the coded beam 119 by the first head mounted device, detecting it by a beam detector 216 of the identified second head mounted device. The identification circuit further comprises logic to decode the coded beam so as to identify the coded beam transmitter and its coding information.

Further Embodiments

Figure 4A:
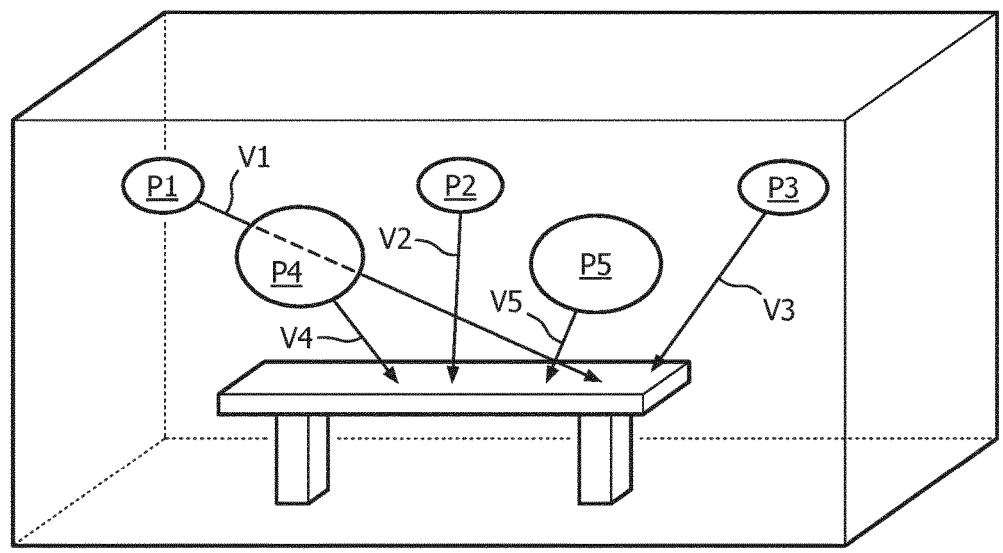
FIG. 4A shows a practical embodiment of the communication system in a surgery room.

FIG. 4A shows a practical embodiment in a surgery room, where head mounted devices are used with corresponding display devices and wearable cameras. Doctors and nurses in the operation room may wear these devices. The devices capture an image or video stream of what they see, from their perspective, also called a 'view'. In addition, the device captures its location within the operation room (e.g. position P1 . . . 5 in x, y, z coordinate) and the direction in which the person is looking described as a path starting from point P (e.g. vector V1 . . . 5 in x, y, z coordinates).

Determining the position P of the mobile camera in the space can be done in various ways using available indoor positioning systems, for example using radio, optical, or acoustic means (e.g. coded light, Wi-Fi, or a combination of technologies). The viewing direction can be determined using the on-board sensors of the wearable camera device (accelerometer, gyroscope). Alternatively, sensors are integrated in the environment (e.g. operating table) that detect the position of the head mounted device relative to the object in the environment (e.g. through line-of-sight).

Video processing may also be an option whereby the central processor can assess the content of the view and compare this to other views, thereby finding similarities and differences. This will enable the multiple views to be mapped based on content.

Figure 4B:
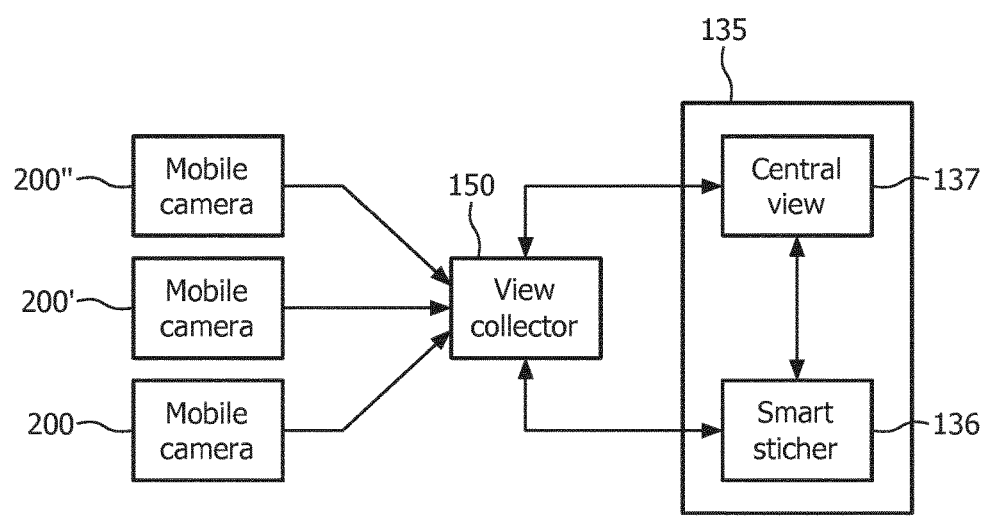
FIG. 4B forms a further example of a communication system that receives capturing information.

The view, the location P and direction V information are transmitted to a central data collector 150 as shown in FIG. 4B. This data collector stores the incoming data. Several components can request data from the data collector.

FIG. 4B forms a further example how communication system 100 receives capturing information from a plurality of head mounted device wearers each having capturing device or mobile camera 200 . . . 200" and communicating with a central view collector device 150 that receives multiple views. The collector device 150 is in communication with augmented reality module 135, that is able to provide multiple views, and has program logic arranged to provide aggregated views by stitching a viewpoint with another viewpoint in augmented reality. These aggregated views are preferably rendered in a central control space or locally at the mobile camera devices 200. To this end, augmented reality module 135 is provided with view rendering logic 136, in particular for rendering a multiple views by a central viewer 137. For example, a doctor can indicate the object that he wants to see and from which angle and the stitching module accordingly selects one or more views from one or more capturing devices 200 . . . 200" that best matches the needs of the doctor. In this way, also, post-procedural evaluations of surgeries can be improved, or staff may be trained in surgical procedures from different perspectives. The central viewing system 150 can also support remote supervision/support i.e. when the operation is guided by a specialist who could not be present himself/herself but could guide doctors at the site. The specialist can then use the aggregated view to have a full picture of the operation as well as detailed view by switching between different mobile camera views.

Central viewer 137 may allow a person typically in an observation or control room to request individual views or aggregated views. In addition to the head mounted device display, such may also be centrally displayed on a 2D display. For example, an observer can specify to the central viewer which perspective he wants to take, e.g. by using a joystick, keyboard, mouse or by using gesture control or head or eye movements detected by more advance input technologies such as eye tracker, head tracker, etc. It is also possible to render the views on a 3D display, for example on an auto-stereoscopic omnidirectional display, to allow observers to easily move around the display to see the object of interest from all angles.

The invention claimed is:

1. A communication system for communication among a plurality of users of wearable devices, wherein each of said wearable devices is arranged to capture a viewpoint of a user of a respective one of the wearable devices, said system comprising:
   a registering circuit arranged to register a predefined user gesture called identifying gesture, thereby identifying the viewpoint of a user of a first of the wearable devices;
   an identification circuit arranged to identify the viewpoint of a user of the first of the wearable devices by the registering circuit of a second of the wearable devices;
   an exchange circuit arranged to cause the first of the wearable devices to exchange a viewpoint captured by the first of the wearable devices with the second of the wearable devices;
   a projecting circuit arranged to project the exchanged viewpoint to a user of the second of the wearable devices;
   a physiological signal monitoring module comprising physiological signal detectors and program logic to convey physiological signal information from the physiological signal detectors to the exchange circuit;
   wherein the exchange circuit is arranged to exchange the identified viewpoint captured by the first of the wearable devices with the second of the wearable devices when a conveyed physiological signal value exceeds a threshold value;
   wherein the plurality of wearable devices includes at least three wearable devices configured to exchange viewpoints of a third of the wearable devices; and
   wherein the viewpoint of each of the wearable devices is different from the viewpoints of the other wearable devices.

2. The communication system according to claim 1, wherein said first and second wearable devices are provided with the identification circuit, said exchange circuit, said registering circuit and said projecting circuit; wherein the projecting circuit comprises an augmented reality module arranged to stitch the exchanged viewpoint with a viewpoint of a user of the second wearable device in augmented reality such that the user views a plurality of the viewpoints that are projected and viewed concurrently on the second wearable device.

3. The communication system according to claim 2, wherein the augmented reality module comprises program logic to display said conveyed physiological signal information in addition to the concurrently displayed viewpoints of the first and second wearable devices.

4. The communication system according to claim 2, wherein the registering circuit of the second wearable device is arranged to register a predefined user hand gesture called exchange gesture, thereby causing the exchange circuit of the second wearable device to exchange the captured viewpoint of the first wearable device to the second wearable device.

5. The communication system according to claim 2, wherein the registering circuit comprises a gaze detection device equipped with an analyze circuit for analyzing a gaze direction of a user of the second wearable device; and a circuit to identify the first wearable device when the circuit detects that said gaze direction coincides with a location of the first wearable device.

6. A communication system comprising:
   a plurality of wearable devices, each wearable device being configured to view a patient from a different viewpoint;
   each wearable device including an identification circuit configured to identify a viewpoint of a corresponding user indicating a view that the corresponding user has of a patient;
   a gaze detection device configured to identify when one of the wearable devices is gazing in a direction of another of the wearable devices;
   each of the wearable devices including a directed coded beam transmitter and a coded beam detector, such that when a directed coded beam is transmitted from one of the wearable devices and detected by the beam detector of another of the wearable devices, an identification circuit of the another wearable device is configured to decode the coded beam so as to identify the coded beam transmitter of the one of the wearable devices;
   an exchange circuit arranged to cause one of the first wearable devices to exchange the viewpoint captured by the one of the wearable devices with the another of the wearable devices;
   each wearable device including:
   a projecting circuit arranged to project an exchanged viewing from the one of the wearable devices to be displayed to a user of the another of the wearable devices,
   such that in response to a first directed coded transmitted by the coded beam transmitter of a first wearable device being received by the beam receiver a second wearable device;
   a physiological signal monitoring module comprising physiological signal detectors and program logic to convey physiological signal information for the physiological signal detectors;
   wherein the exchange circuit is arranged to exchange the identified viewpoint captured by the first wearable device with the second wearable device and the projecting circuit of the second wearable device projects the viewpoint of the first wearable device to the user of the second wearable device when a conveyed physiological signal value exceeds a threshold value.

7. The communication system according to claim 5, wherein the physiological signal information includes pupil dilation and the gaze detection device comprises program logic arranged to perform pupil analysis of a user of the wearable device to determine a direction that the user is gazing.

8. A method of communication for use in hospitals; in particular in intensive care units and emergency rooms or operating rooms, comprising:
- capturing, by a first wearable device, a viewpoint of a user of the first wearable device wearer;
- identifying, by a second wearable device, the viewpoint of the first wearable device;
- conveying physiological signal information;
- causing the first wearable device to exchange the captured viewpoint with a second wearable device when a conveyed physiological signal value exceeds a threshold value; and;
- providing the exchanged viewpoint to a user of the second wearable device wearer.

9. The method of communication according to claim 8, further comprising stitching the exchanged viewpoint from the first wearable device with a viewpoint of the second wearable device in augmented reality and projecting the stitched viewpoints of the first and second wearable devices to the user of the second viewable device, the viewpoints of the first and second wearable devices being different.

10. The method of communication according to claim 8, further comprising augmenting the exchanged viewpoint with physiological signal information displayed by the first wearable device.

11. The method according to claim 8, wherein the first wearable device wearer is caused to exchange the captured viewpoint with a second wearable device wearer by registering a predefined user hand gesture called exchange gesture thereby causing the first wearable device wearer to exchange the captured viewpoint to a second wearable device wearer in response to the exchange gesture.

12. The method according to claim 8, wherein a viewpoint of the first wearable device is identified by gaze detection of the second wearable device.

13. An interactive communication system for a plurality of wearable device viewpoint capturing devices interconnected by communications paths for use in hospitals; in particular in intensive care units and emergency rooms or operating rooms and on at least two of which devices viewpoints can be captured; comprising:
- means associated with at least one of said wearable devices for capturing, by said first wearable device, a viewpoint of a first wearable device wearer; and
- means associated with at least another of said wearable devices for identifying, by said another wearable device, the viewpoint of the first wearable device;
- means for conveying physiological signal information;
- means for causing the first wearable device wearer to exchange the captured viewpoint with a second wearable device wearer when a conveyed physiological signal value exceeds a threshold value; and;
- providing the exchanged viewpoint by the second wearable device as an exchanged viewpoint to the second wearable device wearer.

14. A non-transitory computer-readable medium carrying computer program logic arranged for executing on an augmented reality device and arranged to put into effect the method of claim 8.

15. The method according to claim 8, wherein identifying the viewpoint of the first wearable device includes:
- with the first wearable device, transmitting a coded detector beam;
- with the coded beam identifying the first wearable device and also with the coded beam, determining a gaze direction of the user of the second wearable device.

16. The communication system according to claim 13, wherein the means associated with the at least another wearable device for identifying the viewpoint of the first wearable device includes a coded beam detector configured to detect a coded beam transmitted by the first wearable device and wherein the at least another of the wearable devices further includes means for stitching the viewpoint of the first wearable device with a viewpoint of the at least another of the viewable devices.

* * * * *